United States Patent [19]

Marionnet

[11] Plant 4,381

[45] Feb. 20, 1979

[54] STRAWBERRY PLANT

[75] Inventor: André Marionnet, Soings en Sologne, France

[73] Assignee: Jeanne Marionnet-Rabier, Soings en Sologne, France

[21] Appl. No.: 834,836

[22] Filed: Sep. 19, 1977

[30] Foreign Application Priority Data

Oct. 4, 1976 [FR] France ..... 1164

[51] Int. Cl.[2] ..... A01H 5/03

[52] U.S. Cl. ..... Plt./49

[58] Field of Search ..... Plt./49

*Primary Examiner*—Robert E. Bagwill

*Attorney, Agent, or Firm*—Browdy and Neimark

[57] ABSTRACT

A new and distinct variety of strawberry plant is characterized by being a continuously bearing and very productive variety with the particularity of having a rigid floral stem.

2 Drawing Figures

1

This invention relates to a distinctly new strawberry variety obtained by natural cross-breeding of seedlings carried out in 1972 at Soings en Sologne in France. Asexual reproduction from the original mother plant was carried out by splitting of the roots, division of the meristem and in vitro micropropagation.

The physiological characteristics are as follows: The seasonal blooming is fairly early. The season of maturity is fairly early. The remontance is continuous. Sensitivity to bruises is fairly sensitive. The firmness of the pulp is medium. The taste of the fruit is normal.

The recommended type of culture is plain field and amateur gardens.

The variety is characterized by its uninterrupted production and abundance of fruit, and by the rigidity of the floral stem.

Figure 1:
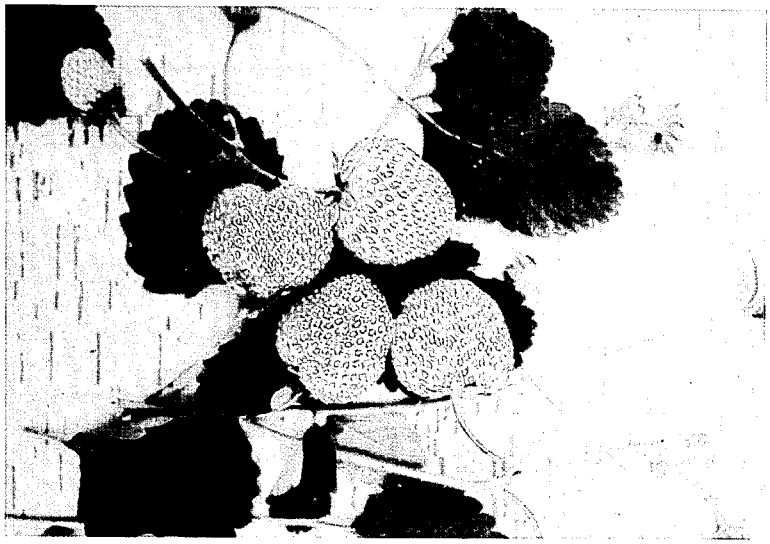
FIG. 1 shows the fruit including the characteristic shape of the fruit.
Figure 2:
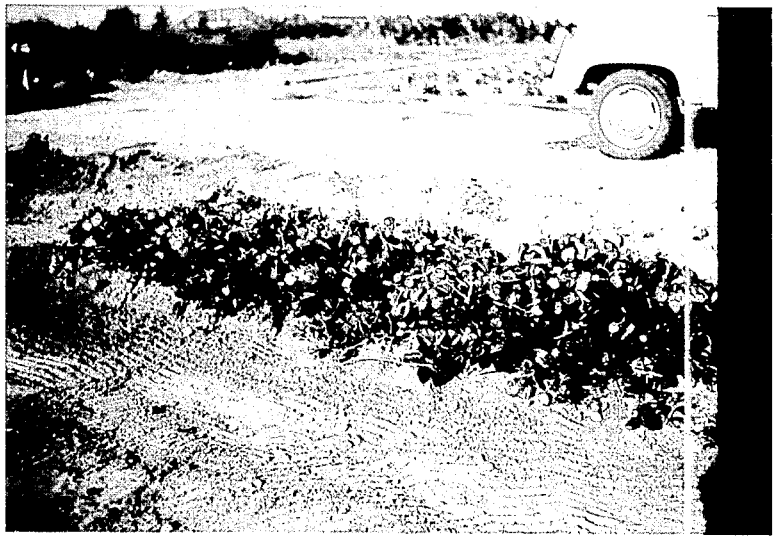
FIG. 2 is a view showing the strawberry plants in cultivation.

The characteristics of the strawberry plant in accordance with the present invention are summarized on the following table:

| MORPHOLOGICAL CHARACTERISTICS | DESCRIPTION |
|---|---|
| GROWTH OF THE PLANT | More or less spread out |
| Leaf: a) Stem | |
| Angle of Leaf Stem to Main Stem | 90° ~ 120° |
| Shape at the Base | V-shaped |
| Pilosity of the Upper Face | Medium |
| Color | Dark Green |
| Brilliance | Brillant |
| General Shape (terminal foliage) | Spoon-Shaped |
| Ratio between Length/Width | 1.05 to 1.20 |
| Pilosity | Medium |
| Position of Hair | Perpendicular |
| FLOWERS | |
| No. of Petals: Elder Flowers | 5 to 9 |
| No. of Petals: Younger Flowers | More than 6 |
| Ratio of Length/Width of | As Wide as Long |

2

-continued

| MORPHOLOGICAL CHARACTERISTICS | DESCRIPTION |
|---|---|
| Petals | |
| Angle at the Stem of Petals | Obtuse |
| Position of Hair on the Peduncle | Perpendicular |
| Relative Position of Flowers/ Foliage | Same Level as the Leaves |
| Ratio of Length of Sepalules (s)/Sepals (S) | s = S |
| Ratio of Length of Sepals (S)/Petals (P) | S > P |
| Stamens | Present |
| FRUIT | |
| Size | Medium |
| Length of Peduncle | Medium |
| Shape of the Elder Fruit and the Younger Fruit | Similar |
| Shape of the Young Fruit | Round |
| Ratio of Width (1)/ Height (H) (Young Fruit) | 1 > H |
| Size of First Ripening Fruit | Medium |
| Position of the Achenes | Slightly Bulging |
| Zone of Achenes | Weak or None |
| Overall Color | Homogeneous |
| Color of the Pulp | Vivid Red |
| Color of Skin | Medium Red (HCC 820) |
| Brilliance | Brilliant |
| Position of the Calyx and the Calicle | One Leaning, the Other One Upright or Down |
| STOLONS (Well Developed) | |
| Number | About 20/year |
| Color at Insolation | Purple |
| Color of Those Facing the Ground or under the Foliage | Purple |
| Size | Large |
| Position of hair | Perpendicular |
| PHYSIOLOGIC CHARACTERISTICS | |
| Blooming Season | Fairly Early |
| Maturity Season | Fairly Early |
| Remontance | Continuously Remontant |
| Sensitivity to Bruises | Fairly Sensitive |
| Firmness of the Pulp | Medium |
| Taste of the Fruit | Normal |

What is claimed is:

1. A new and distinct variety of strawberry plant substantially as herein shown and described, characterized by the fact that it is a continuously bearing (practically uninterrupted over six months with significant production on the annual stolons) and very productive variety with the peculiarity of having a rigid floral stem.

* * * * *